United States Patent
Kimmig et al.

(10) Patent No.: US 12,109,423 B2
(45) Date of Patent: Oct. 8, 2024

(54) METHOD FOR PRODUCING A MEDICAL IMPLANT

(71) Applicant: Neuroloop GmbH, Freiburg (DE)

(72) Inventors: Fabian Kimmig, Freiburg (DE); Tim Boretius, Freiburg (DE); Florian Adami, Freiburg (DE)

(73) Assignee: Neuroloop GmbH, Freiburg (DE)

( * ) Notice: Subject to any disclaimer, the term of this patent is extended or adjusted under 35 U.S.C. 154(b) by 616 days.

(21) Appl. No.: 17/438,563

(22) PCT Filed: Mar. 2, 2020

(86) PCT No.: PCT/EP2020/055465
§ 371 (c)(1),
(2) Date: Sep. 13, 2021

(87) PCT Pub. No.: WO2020/182525
PCT Pub. Date: Sep. 17, 2020

(65) Prior Publication Data
US 2022/0143413 A1   May 12, 2022

(30) Foreign Application Priority Data
Mar. 11, 2019   (DE) .................... 10 2019 203 273.7

(51) Int. Cl.
*B29C 70/88*   (2006.01)
*A61N 1/375*   (2006.01)
(Continued)

(52) U.S. Cl.
CPC ...... *A61N 1/3754* (2013.01); *B29C 45/14639* (2013.01); *B29C 70/72* (2013.01); *B29C 70/88* (2013.01)

(58) Field of Classification Search
CPC ..................................................... B29C 70/72
See application file for complete search history.

(56) References Cited

U.S. PATENT DOCUMENTS

| 2003/0144707 A1 | 7/2003 | Ruben et al. |
| 2008/0033500 A1 | 2/2008 | Strother et al. |
(Continued)

FOREIGN PATENT DOCUMENTS

| DE | 4131259 A1 | 3/1993 |
| DE | 102012010901 A1 | 12/2012 |
(Continued)

OTHER PUBLICATIONS

Machine translation of WO 2020182525, retrieved from EPO database Jun. 25, 2024 (Year: 2024).*

(Continued)

*Primary Examiner* — Timothy Kennedy
(74) *Attorney, Agent, or Firm* — Fitch, Even, Tabin & Flannery LLP

(57) ABSTRACT

A method for the production of a medical implant, comprising a head section, which has at least one blind hole-type recess of an electrical plug-in contact socket, along which is arranged at least one electrically conductive contact element, together with a supply section, which is fixedly connected to the head section, and which comprises at least one electrical component, which is one of at least one microcontroller, and an electrical energy source, which are electrically connected to the at least one electrically conductive contact by way of at least one electrical conductor.

9 Claims, 2 Drawing Sheets

(51) Int. Cl.
*B29C 45/14* (2006.01)
*B29C 70/72* (2006.01)

(56) References Cited

U.S. PATENT DOCUMENTS

2012/0193119 A1  8/2012  Kempf et al.
2016/0166825 A1  6/2016  Henschel et al.
2020/0360701 A1  11/2020  Kimmig et al.

FOREIGN PATENT DOCUMENTS

| DE | 202013012073 U1 | 4/2015 |
| DE | 102017222364 A1 | 6/2019 |
| EP | 2082780 A2 | 7/2009 |
| EP | 2134418 B1 | 6/2012 |
| WO | 2017/029615 A1 | 2/2017 |

OTHER PUBLICATIONS

International Search Report for PCT/EP2020/055465, mailed Jun. 24, 2020; English translation submitted herewith (5 pgs.).

\* cited by examiner

METHOD FOR PRODUCING A MEDICAL IMPLANT

CROSS-REFERENCE TO RELATED APPLICATIONS

Reference is made to International Application No. PCT/EP2020/055465, filed Mar. 2, 2020, which claims priority to German Patent Application No. 10 2019 203 273.7, filed Mar. 11, 2019, the contents of which are incorporated herein by reference in their entirety.

BACKGROUND OF THE INVENTION

Field of the Invention

The invention relates to a method for the production of a medical implant, comprising a head section, which has at least one blind hole-type recess designed in the manner of an electrical plug-in contact socket, along which is arranged at least one electrically conductive contact element, and a supply section, which is fixedly connected to the head section, and comprises at least one electrical component, preferably in the form of at least one of a microcontroller, and an electrical energy source, which are electrically connected to the at least one electrically conductive contact element by at least one electrical conductor.

Description of the Prior Art

Implantable medical devices for the purpose of electrical stimulation of local intracorporeal regions, in short, implantable pulse generators (IPGs), for example for heart therapeutical defibrillation, pacemaker, and resynchronization, applications, for neurostimulation therapeutical measures, such as spinal cord stimulation, brain stimulation, or vagus nerve stimulation, to name but a few, generally speaking have a self-contained housing, in which are included components for electrical pulse generation, such as at least one electrical energy source, and an electrical circuit structure connected to the latter. In addition, a so-called head section is attached to the housing, in which the head section is included in an electrical contact arrangement, electrically connected to the energy source, or to the electrical circuit structure, into which can be introduced a connector arrangement that is connected in a manner impermeable to fluids to the head section, which connector arrangement is in established contact with electrical supply and return lines for purposes of the intracorporeal local application of the electrical stimulation signals, and, if necessary, the supply of intracorporeally locally tapped electrical signals to the electrical circuit structure that is located in the housing.

In EP 2 134 418 B1 there is described a generic head section of an implantable medical device, which comprises two head section housing-halves, which can be joined together along a joining seam, into which semi-cylindrical recesses are inserted in each case in a serial sequence, spaced apart by partition walls, into which recesses are inserted electrically and conductive contact ring elements, and electrically insulating sealing rings, in each case in a serially alternating sequence. The head section, assembled from the two head section housing halves, comprises an arrangement of coaxially aligned and electrically insulated contact ring elements, for the establishment of electrical contact with which a lateral access is provided in the head section, through which access an electrical connector arrangement can be introduced, in a manner impermeable to fluids, into a cavity surrounded by all the annular contact ring elements.

DE 10 2012 010 901 A1 discloses a method for the positioning and holding electrical contacts and seals within a head section for the establishment of electrical contact with a medical implantable device. A blind hole is introduced into one side of the head section housing, which is made of a biocompatible and electrically insulating material, into which housing electrically conductive contact rings and annular sealing elements are introduced in an alternating sequence, which together surround a cavity, into which a pin-form connector arrangement can be introduced. Each of the individual annular contact rings is connected within the head section by an electrical connection line to electrical components located within the housing of the medical implantable device.

DE 20 2013 012 073 U1 discloses a connector bore module, for the assembly of contact rings and sealing elements which are arranged in an alternating sequence along a pin-form assembly tool. By use of a clamping device, all contact rings and sealing elements seated along the assembly tool, are clamped against each other by the application of an axial clamping force. For the purpose of preserving the clamping force, a sleeve is used, which is seated in an axially fixed manner on the assembly tool by a grub screw, and which, together with an assembly tool head at the end, bounds the arrangement of contact rings and sealing elements axially on both sides. In this clamped state, the arrangement is encapsulated in a curable casting compound, which takes up the clamping force in the solidified state.

Methods for the production of a medical implant are of known art from US published patent applications 2016/0 166 825 and 2008/0 033 500. In both cases, the supply section and the head element are encapsulated in a casting compound monobloc, in at least a final production step.

The US published patent application 2003/0 144 707 discloses an implantable medical device with a surface contact arrangement.

DE 10 2017 222 364 A1 describes a method for the production of a head section of an implantable medical device, with a plug-in contact socket, in which a serial sequence of contact ring elements and electrically insulating sealing rings are arranged. An assembly tool is used for the mechanical clamping together of the annular elements. The tool is removed after the completion of the medical device, wherein the clamping together of the annular elements by force is taken up by the solidified plastic matrix of the head section.

SUMMARY OF THE INVENTION

The invention is a further development of a method for the production of a medical implant, comprising a headsection, which has at least one blind hole-type recess providing an electrical plug-in contact socket, along which is arranged at least one electrically conductive contact, and a supply section, which is fixedly connected to the head section, and comprises at least one electrical component, which preferably is at least one of a microcontroller, and an electrical energy source. These components are electrically connected to the at least one electrically conductive contact by way of at least one electrical conductor, such that a procedural, time and cost saving providing effort for the production of both individually assembled implants, and also implants produced in large numbers, is significantly reduced. It is also of particular interest that the production quality, together with the fluid impermeability and the associated service life of the implants, should meet the highest demands. Since up to the present time it has been necessary to manufacture the head section and the supply section in separate building processes for technical reasons, special attention is paid to the joining of the head section and the supply section so as to be able to implement a durable joint that is impermeable to fluids, in accordance with the above-mentioned production requirements.

Of central importance in the production of generic medical implants is the design of the joint between the head section and the supply section, which in accordance with the invention is a material bond, that is, monolithical and ensures a durable joint between the head section and the supply section that is impermeable to fluids. Irrespective of the particular technical design of the head section and the supply section, both of which are encapsulated in a biocompatible casting compound by way of casting, both the head section and the supply section are joined by material bonding to two opposing faces of a connecting plate, which is referred to herein as a fixing plate, and is constructed as a curable casting material, in which material both the head section and the supply section are encapsulated.

For purposes of electrically connecting the at least one electrically conductive contact element included in the head section to the microcontroller and the electrical energy source preferably contained in the supply section, it is necessary to guide the at least one electrical conductor through the fixing plate that connects the head section to the supply.

The method in accordance with the invention first provides for the production of the fixing plate, which has an upper face and a lower face, and is manufactured as a semi-finished product by a casting process using a curable casting compound. During the casting process, at least one electrical conductor, preferably in the form of a wire section, is oriented and arranged orthogonally with respect to the forming upper and lower faces of the fixing plate, so that the conductor is fixedly connected to the fixing plate after the curing of the casting compound, and projects beyond it, on both sides of the upper and lower faces of the plate.

Depending on the number of electrically conductive contact elements present within head a the section, corresponding number of electrical conductors, protruding through the fixing plate, must be provided. For this purpose, the electrical conductors protruding through the fixing plate, orthogonally with respect to the upper and lower faces of the plate, are distributed in the fixing plate in accordance with the spatial arrangement of the electrically conductive contacts within the head section. As an alternative to the embedding of the electrical conductor in the course of the casting process, it is also possible to produce the fixing plate separately from the electrical conductors by way of the casting process. In this case, the electrical conductors are subsequently inserted into fine holes protruding through the fixing plate, and are wetted with an adhesive, for example with a drop of epoxy, which fixes the conductors in position as occurs, and is the same material as the head section.

For the production of the supply section, a casting mold is used in a manner known per se, which determines the outer shape and form of the supply section. In the preparation for the casting process, the at least one electrical component, which preferably is at least one of a microcontroller and an electrical energy source, is positioned inside the casting mold and connected to the at least one electrical conductor. In accordance with the invention, the casting mold is designed with the fixing plate being prepared as a semi-finished product to be integrated into the casting mold. The lower face forms part of the surface bounding of the casting mold. Subsequently, the at least one electrical conductor projects beyond the lower face of the plate, together with the at least one electrical component, which are encapsulated in the curable casting compound.

In the course of the casting process, the casting compound fills the prepared casting mold and encloses the components arranged therein, wherein the flowable casting compound wets the lower face of the fixing plate serving as part of the casting mold surface, with the formation of a monolithic material bond.

After the casting compound has cured, the supply section is removed from the casting mold together with the fixing plate which is fixedly attached to the supply section which is fixedly connected to it.

For the production of the head section, the at least one electrically conductive contact must first be provided, and connected to the at least one electrically conductive projecting beyond the upper face of the fixing structure.

Usually, the head section provides a multiplicity of electrically conductive contacts, which are contact ring elements, and in the alternate are a coaxial in an axial serial sequence having electrically insulating, elastically deformable sealing rings which are force-fitted against each other under an axial clamping force. A preferred design of such a prestressed stacking arrangement of contact ring elements, which is integrated in a head section, is explained in more detail with reference to the following figures.

The electrical conductors protruding above the upper face of the fixing plate are in electrical contact with the respective electrical contacts which are provided within the head section, preferably by a soldering, bonding, gap welding, or friction welding, process. Optionally, further electrical structures can be introduced into the head section, for example an antenna, which can be connected to corresponding electrical components within the supply section. Furthermore, the at least one contact electrically connected to the electrical conductor is encapsulated in the curable casting compound such that a materially bonded connection to the upper face of the fixing plate is formed. The casting process for the production of the head section can be carried out before, during or after the manufacture of the supply section.

As in the case of the casting process for the production of the supply section, a monolithic material bond that is impermeable to fluids is also formed between the upper face of the fixing plate and the curable casting compound on the head section-side, so that all electrical components that are cast around the head section, the fixing plate and the supply section by use of the curable casting compound are completely surrounded by the casting compound in a manner impermeable to fluids, without any boundary surfaces.

Biocompatible plastics or epoxy resins are suitable as the casting compounds for the production of the head section, the fixing plate and the supply section.

BRIEF DESCRIPTION OF THE DRAWINGS

Without any limitation, the invention is described in an exemplary manner below by way of examples of embodiment, with reference to the drawings. Here.

DETAILED DESCRIPTION OF THE INVENTION

Figure 1:
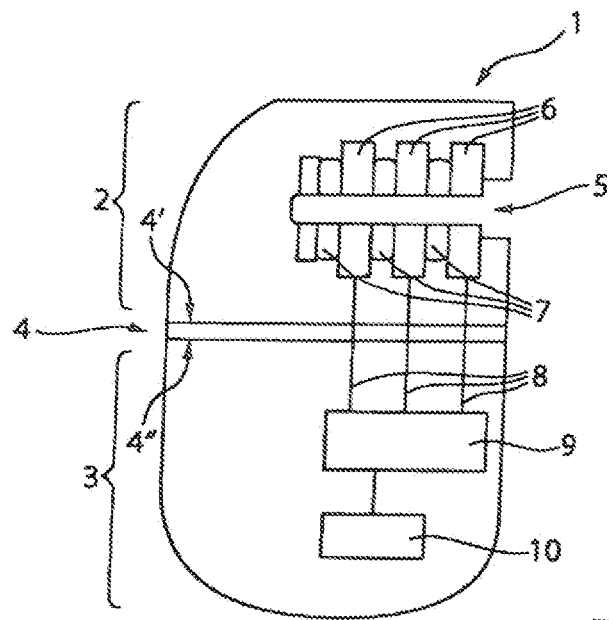
FIG. 1 shows an illustration of a medical implant designed in accordance with the invention.

FIG. 1 shows a medical implant 1 manufactured in accordance with the invention, comprising a head section 2, a supply section 3, and a fixing plate 4, the upper face 4' of which is joined to the head section 2, and the lower face 4" of which is joined to the supply 3 by material bonding, which is monolithical.

The head section 2 has a blind hole-type recess 5 providing an electrical plug-in contact socket, along which are arranged electrical contact elements 6 which are contact ring elements in a serial sequence, in each case axially spaced apart by interposed electrically insulating sealing rings 7. The serial sequence of contact ring elements 6 and sealing rings 7 is subjected to an axial clamping force F, by use of which the contact ring elements 6 and the sealing rings 7 are clamped together in a manner impermeable to fluids. For the electrical signal and energy supply, the electrical contact rings 6 are connected by wire electrical conductors 8 to a microcontroller 9 within the supply section 3, and to an electrical energy source 10 electrically connected to the microcontroller 9. The electrical energy source 10 can be designed as a battery, accumulator, biofuel cell, or in the form of an inductive coupling loop for a contactless inductive transfer of energy. Needless to say, alternative or further electrical components can be included in the supply section 1.

All components of the medical implant 1 are in each case encapsulated in a biocompatible casting compound monobloc, which preferably is a plastic or resin compound, and most preferably is an epoxy resin compound.

Figure 2:
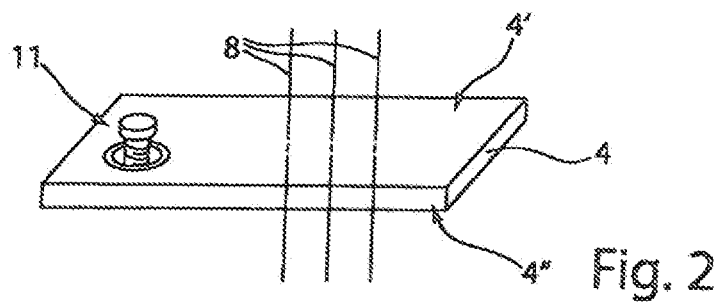
FIG. 2 shows an illustration of a fixing plate with protruding electrical conductors.

For the production of the medical implant 1 illustrated in FIG. 1, the fixing plate 4 is manufactured from a biocompatible casting compound in the course of a casting process as shown in FIG. 2, wherein the wire-form electrical conductors 8 project through the fixing plate 4 orthogonally with respect to the top 4' and bottom 4" of the plate. Optionally, a mechanical connector 11 is introduced within the fixing plate 4, preferably in the form of a threaded nut with a screw that can be introduced therein, for the stationary fixing of the head section-side serial sequence of sealing rings 7 and contact ring elements 6. In this respect see also the contact ring/sealing ring element arrangement 14 in FIG. 14, which can be equipped with an appropriate mechanical holder (not shown), for an additional fixing to the fixing plate 4 by a screw connection 11.

The fixing plate 4, which is designed as a separate semi-finished product, with the wire-form electrical conductor structures 8 attached therein, serves furthermore as part of the surface of a casting mold 12 for the production and design of the supply section 3. First of all, it is necessary to electrically connect the electrical conductors 8, which protrude beyond the plate lower face 4", to the microcontroller 9 as shown, as well as to the electrical energy source 10. The electrical connections can be made before or after the insertion of the fixing plate 4 into the casting mold for forming a boundary for the latter.

Figure 3:
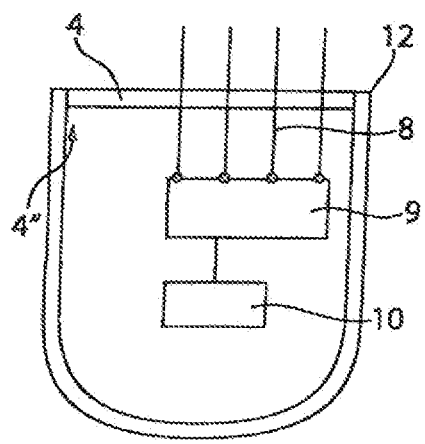
FIG. 3 shows a casting mold for the production of the supply section.

FIG. 3 shows the fixing plate 4 inserted into the casting mold 12. The lower face of the plate 4" is capable of bounding the interior of the casting mold 12 in a manner impermeable to fluids. In what follows, the casting mold 12 is completely filled with a biocompatible curable casting compound. The biocompatible curable casting compound used for filling the casting mold 12 is identical to that of which the fixing plate 4 is made, so that a materially bonded, monolithic connection is formed between the lower face 4" of the fixing plate 4 and the casting compound.

Figure 4:
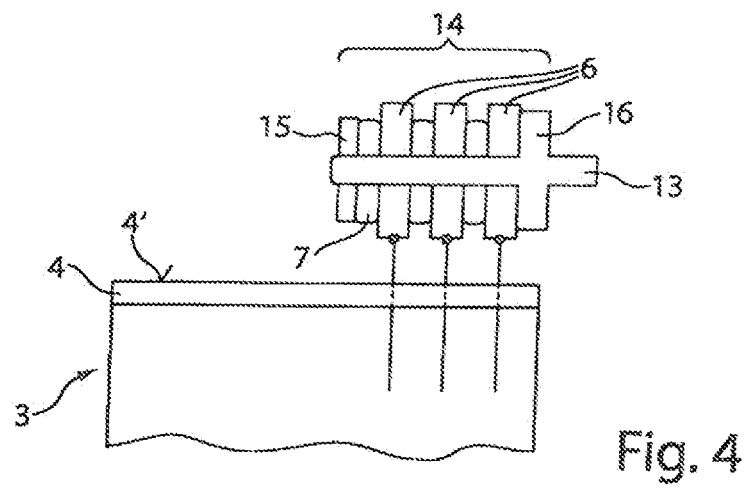
FIG. 4 shows the electrical connection of the electrical conductors to an arrangement of contact ring elements.

Following the casting process, electrical contacts are established between the electrical conductors 8 projecting beyond the upper side 4' of the fixing plate 4 and the contact ring 6, as shown in FIG. 4.

The axial stack 14 illustrated in FIG. 4, has electrical contact rings 6 and interposed sealing rings 7, which is a semi-finished product, with a rod-shaped assembly tool 13, along which the electrically conductive contact rings 6, and the interposed electrically insulating sealing rings 7, made of an elastomeric material, are arranged in an axially alternating sequence. On both sides of the axial stack 14, composed of the alternating sequence of contact rings 6 and sealing rings 7, fasteners 15 and 16 are in each case attached along the rod-shaped assembly tool 13. In the case of the fasteners 16 shown in FIG. 4, a mechanical stop is formed which is integrally connected to the assembly tool 13, which is otherwise rod-shaped in design. The stop is designed as a plate or disc, to which the axial stack 14 is directly adjacent on one side. The fasteners 15, which are opposed to the stop along the axial stack 14, is axially movable along the rod-shaped assembly tool 13, and also has a locking mechanism, which fixes the fasteners 15 in an axially secure manner relative to the rod-shaped assembly tool. The fasteners 15 preferably are a nut or a plate with an internal thread, which engages with an external thread (not shown), provided at one end along the rod-shaped assembly tool 13.

In order to apply the clamping force, oriented axially to the rod-shaped assembly tool 13, which clamps the alternating sequence of contact ring elements 6 and sealing rings 7 in a force-fit with, or against, each other, it is necessary to rotate the assembly tool 13 relative to the fasteners 15, for example by completely screwing the assembly tool-side external thread into the internal thread of the fasteners 15, as a result of which a defined clamping force acting along the contact ring elements 6 and sealing rings 7 seated on the assembly tool 13 is established.

Figure 5:
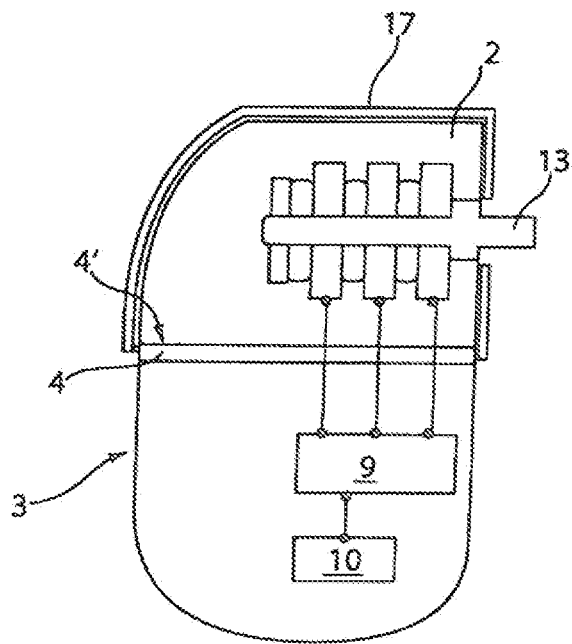
FIG. 5 shows an illustration of the production of the casting compound for the head section.

The axial stack 14 shown in FIG. 4 represents a semi-finished product that can be handled separately, which is inserted into a casting mold 17 as shown in FIG. 5 after appropriate electrical contacts have been established between the electrical conductor structures 8 and the electrical contact rings 6. The casting mold 17 is, as in the case of the casting process according to FIG. 3, partially bounded by the fixing plate 4, which is integrally connected to the casting compound on the supply section-side, i.e. the upper face 4' of the fixing plate 4 closes off the rest of the casting mold 17 in a manner impermeable to fluids. The casting process takes place in the same manner, with the use of the same solidifiable casting compound, as that with which the fixing plate 4 and the cast body of the supply section 3 are made.

After the head section-side casting compound has solidified, the medical implant 1 can be removed from the casting mold 17, and the assembly tool 13 can be separated from the fasteners 15 by rotation. The clamping force prevailing axially between the contact rings 6 and the sealing rings 7 is supported and conserved by the head section-side solidified casting compound. As an alternative to the procedure as explained above, it is also possible to carry out the casting procedure shown in FIG. 5 before, or at the same time as, the casting procedure for the production of the supply section 3 shown in FIG. 3.

LIST OF REFERENCE SIGNS

1 Medical implant
2 Head section
3 Supply section
4 Fixing plate
4' Plate upper face
4" Plate lower face
5 Blind hole recess
6 Electrically conductive contact, contact ring
7 Sealing ring
8 Electrical conductor
9 Microcontroller
10 Electrical energy source, battery
11 Mechanical fastener
12 Casting mold
13 Assembly tool
14 Axial Stack
15, 16 Fasteners
17 Casting mold

The invention claimed is:

1. A method for the production of a medical implant, having a head section, including at least one blind hole recess electrical plug-in contact socket, containing at least one electrical contact, and a supply section, connected to the head section which includes at least one electrical component, that is electrically connected to the at least one electrical contact by at least one electrical conductor, comprising:
   producing a fixing plate comprising a curable casting compound having an upper plate face and a lower plate face in which at least one electrical conductor is fixed and which projects through the upper and lower plate faces;
   positioning the fixing plate in a casting mold in which the lower plate face forms part of a surface of the casting mold;
   establishing electrical contact between at least one electrical conductor and the at least one electrical component, before or after the positioning of the fixing plate, which is part of a surface partially bounding the casting mold; and
   producing the supply section by encapsulating the at least one electrical component and the at least one electrical conductor, which projects beyond the lower plate face, in a curable casting compound, to form a material bond with the lower plate face of the fixing plate.

2. A method according to claim 1, comprising:
casting the fixing plate by introducing the curable casting compound into a casting mold.

3. A method according to claim 2, comprising:
introducing the at least one electrical conductor into the casting mold while the casting is carried out.

4. A method according to claim 3, comprising:
forming at least one hole in a cured fixing plate and passing the at least one electrical conductor through the cured fixing plate and fixing the at least one conductor in the at least one hole by an adhesive.

5. A method according to claim 1, wherein:
the at least one electrical conductor projects beyond the upper plate face and is electrically connected to the at least one electrical contact; and
the at least one electrical contact is fixed to the fixing plate.

6. A method according to claim 1, comprising:
the electrical contacts including a contact ring and alternates in a coaxial and in an axial serial sequence with electrically insulating elastically deformable sealing rings being force fit together with an axial clamping force; and
the contact rings and sealing rings are in a coaxial and an axial serial sequence after an electrical contact is established between the contact rings and at least one electrical conductor projects beyond the upper plate face and is connected to the upper plate face of the fixing plate.

7. A method according to claim 1, comprising:
wherein the at least one electrical contact, is electrically connected to the electrical conductor, is encapsulated in the curable casting compound which forms the head section, to provide a material bond to the upper face of the fixing plate.

8. A method according to claim 1, wherein:
the casting material is a biocompatible epoxy.

9. A method according to claim 1, wherein:
the supply section is an implantable medical device comprising a pulse generator.

* * * * *